United States Patent [19]
Clarkson et al.

[11] Patent Number: 5,902,581
[45] Date of Patent: May 11, 1999

[54] XYLANASE FROM *ACIDOTHERMUS CELLULOLYTICUS*

[75] Inventors: Kathleen A. Clarkson, San Francisco, Calif.; Andrew J. Morgan, Marlborough, United Kingdom; Zhi C. Wang, San Francisco, Calif.

[73] Assignee: Genencor International, Inc., Rochester, N.Y.

[21] Appl. No.: 08/567,382

[22] Filed: Dec. 4, 1995

[51] Int. Cl.⁶ .............................. A61K 38/47; C12N 9/42; C12N 1/20
[52] U.S. Cl. ..................... 424/94.61; 424/94.1; 424/94.6; 435/183; 435/195; 435/209; 435/814; 435/822
[58] Field of Search .................................. 424/94.1, 94.6, 424/439, 442, 94.61; 435/183, 195, 822, 814, 209

[56] References Cited

FOREIGN PATENT DOCUMENTS 94 21 785   9/1994   WIPO .

OTHER PUBLICATIONS

Ritschkoff et al., J. Biotechnology, 32:67–74, 1994.
Uchino et al., Agric. Biol. Chem. 45:1121–1127, 1981.

*Primary Examiner*—Jon P. Weber
*Assistant Examiner*—Janet M. Kerr
*Attorney, Agent, or Firm*—Kirsten A. Anderson; Genencor International, Inc.

[57] ABSTRACT

A purified xylanase produced by *Acidothermus cellulolyticus* is disclosed having a pH optimum of between about 3.6–4.2 and a molecular weight of between about 50–55 kD as determined by gel filtration. The disclosed xylanase is useful in the bleaching of pulp for the production of paper and in treating feed compositions.

3 Claims, 2 Drawing Sheets

XYLANASE FROM *ACIDOTHERMUS CELLULOLYTICUS*

BACKGROUND OF THE INVENTION

1. Field of the Invention

The present invention is related to a novel xylanase composition and a method for its production. Specifically, the invention is related to a purified xylanase composition derived from Acidothermus sp., and particularly *Acidothermus cellulolyticus*, and the use of that enzyme in bleaching pulp and paper and treating feed compositions.

2. State of the Art

Xylanases are known to be produced by a number of different microorganisms. Several different xylanolytic enzymes are generally produced by a microorganism, each of the xylanases acting to attack different bonds in the wood complex. Attempts to use enzymes derived from both fungal and bacterial sources in industrial processes, e.g., for enhancing delignification and brightening while lowering or eliminating the use of chlorine in the bleaching of lignocellulosic pulp in the paper industry or for improving the value of animal feed have been described in the literature.

Xylanases, e.g., endo-β-xylanases (EC 3.2.1.8), which hydrolyze the xylan backbone chain, have been studied for their use in bleaching lignocellulosic material. For example, in U.S. Pat. No. 5,179,021, the combination of xylanase and oxygen treatment in the bleaching of pulp is disclosed as being particularly useful. In PCT Application Publication No. WO 92/03541, a method of dissolving hemicellulose with hemicellulases derived from the fungus *Trichoderma reesei* is disclosed. The search for xylanases, however, has focused on thermophilic and alkalophilic xylanases which are useful under pulp bleaching conditions utilizing high temperatures and alkali. However, the use of oxygen or ozone bleaching generally occurs at a lower pH. Accordingly, it would be advantageous to discover a low pH xylanase which has significant activity at high temperatures.

Recently, several thermophilic xylanases from fungal and bacterial microorganisms have been identified. For example, a thermophilic xylanase has been isolated from Actinomadura reclassified as Microtetraspora having an optimal pH of 6.0–7.0 and temperature range of 70–80° C. (Holtz, C. et al Antonie van Leewenhoek 59:1–7, 1991). EP 473 545 discloses that the bacterial strain *Thermomonospora fusca* produces thermostable xylanases active at temperatures 10–90° C., preferably, 50–80° C. over a wide pH range, i.e., from about 5–10, with the more preferred range between 6.6–9.5. In addition, WO92/18612 discloses a xylanase enzyme derived from the genus, Dictyoglomus, having activity over a broad pH range (5.0–9.0) and thermostability at temperatures ranging from 60–90° C. The thermophilic cellulolytic bacteria *Acidothermus cellulolyticus* is described in Mohagheghi et al., Int. J. Systematic Bact., vol. 36, no. 3, pp. 435–443 (1986), and the production of cellulase is described in Shiang et al., Appl. Microb. Biotech., vol. 34, pp. 591–597 (1991). However, neither reference describes a purified xylanase which may be useful at low pH and high temperature.

Xylanases have also been useful in animal feeds to enable animals to digest the feeds more efficiently. One result of adding xylanase to feed is an improvement in the Feed Conversion Ratio (FCR) of a feed without increasing its cost per unit weight. The FCR of a feed is the ratio of the amount of feed consumed relative to the weight gain of the animal. A low FCR indicates that a given amount of feed results in a growing animal gaining proportionately more weight. This means that the animal is able to utilise the feed more efficiently. One way in which the FCR can be reduced is to improve its digestibility by an animal thereby increasing the nutritional benefit which the animal can derive from it.

However, there are various constraints on the digestibility of the nutritional components of a feed such as its starch, fat, protein and amino acid content. These constraints include:

(i) the viscosity of materials present in the animal's gut. Such viscosity is due, at least in part, to soluble non-starch polysaccharides such as mixed-linked β-glucans and arabinoxylans;

(ii) entrapment of nutrients within the cell walls of the feed, particularly those of the aleurone layer in cereals. Such entrapment is caused by the high levels of non-starch polysaccharides in the cell walls of cereals which are relatively resistant to break-down by the animal's digestive system. This prevents the nutrients entrapped within the cells from being nutritionally available to the animal; and (iii) a deficiency in endogenous enzyme activity, both of the animal and of the gut microbial population particularly in a young animal.

The above problems which interfere with digestibility are particularly noticeable in the case of cereal-based diets, such as those having a high wheat content.

Due to the problem of poor digestibility of nutrients from the feed, it is normally necessary to formulate feeds to contain higher levels of energy and protein providing materials in order to meet the nutritional demands of animals.

There is now a substantial body of evidence showing that incorporating certain (supplementary) enzymes in cereal-based animal feeds can be advantageous in reducing the viscosity of material present in the animal's gut. This reduction can be achieved by enzymes such as xylanases which hydrolyse soluble xylans thereby reducing digesta viscosity which is an important constraint on the process of digestion.

The xylanases which are added as supplements must be stable and active at the pH and temperature conditions found within the gastrointestinal (GI) tract of the target animal. If they are not stable and active when exposed to such in vivo conditions, then they will not be able to reduce digesta viscosity to any significant extent. It is presently known to include xylanases as a supplement in an animal feed derived from fungi such as *Trichoderma longibrachiatum, Aspergillus niger* and *Humicola insolens*. Bedford and Classen (The Journal of Nutrition, vol. 122, pp 560–569) disclose that there is a significant correlation between digesta viscosity measured in vivo in the case of broiler chickens and body-weight gain and FCR values. In the case of wheat and rye-based diets fed to poultry, it was shown that as much as 70–80% of the variations in the weight gain and FCR are based upon differences in intestinal viscosity alone. This highlights the importance of digesta viscosity in cereal-based feeds containing high levels of soluble arabinoxylans. As digesta viscosity increases, it reduces the digestibility of all nutrients by interfering with the diffusion of pancreatic enzymes, substrates and the end products of the digestion process.

However, the use of enzyme supplements, such as xylanase, in animal feed is complicated by the processing requirements for grain supplements. Often, such enzyme supplements are obtained by impregnating the enzyme onto a physiologically acceptable carrier, such as a cereal. The impregnated carrier is mixed with the other components of the feed and then pressed into cubes or pellets for feeding directly to animals. The processes which have been developed make use of relatively high temperatures. This is firstly to improve the efficiency of the manufacturing process and secondly to produce feeds which are free from harmful bacteria, particularly Salmonella. In addition, the use of high temperatures improves the quality and durability of the resulting cubes and pellets, increases the range of ingredients which can be efficiently handled and also increases the level of liquid ingredients, such as fat and molasses, which can be incorporated into the feed.

Processing techniques for feed components currently employ relatively high temperatures for a relatively long period. Further, the mixture is subjected to relatively high pressures during pelleting to increase the durability of the cubes or pellets formed. One of the processing methods which has been developed to improve the nutritional properties of the feed is steam pelleting. This method includes the step of treating the compounded feed with steam to increase its temperature and moisture content. This step is termed conditioning. Conditioning lasts from a few seconds up to several minutes depending on the type and formulation of the feed. The temperature in the conditioner may rise to 100° C. Afterwards, the feed is passed through a pelleting die which causes a rapid increase in its temperature due to friction.

Recently, a new device for pretreatment or conditioning of feeds has been introduced called an expander. This device allows sustained conditioning under pressure followed by pelleting. According to this technique, various feed components which have previously been subjected to steam-conditioning are fed into a compression screw into which more steam is injected, and the mass is then subjected to increasing pressure and shear action and then forced through a variable exit gap. The compressed product, after reduction in particle size, is fed into a standard pelleting press. The dwell time of the feed components in the expander is about 5–20 seconds, and the temperature reached may be as high as 145° C. A compression pressure of about 3.5 MPa is reached, but the build-up of both temperature and pressure is very quick and both fall rapidly as the product is expelled through the exit gap. The use of expanders is advantageous because they effectively eliminate harmful bacteria, particularly Salmonella. Furthermore, it is possible to include relatively high levels of fat and other liquid ingredients in the mixture prior to pelleting. In addition, the cooking and pressure/shear action results in greater starch gelatinisation.

Unfortunately, the high temperature and high pressure processing conditions characteristic of the expander and pelleting technology, particularly when applied in the moist conditions normally encountered during pelleting, are potentially destructive to certain feed components. This is particularly true of any enzymes, including xylanases, which are present. Thus, the prior art enzymes have generally had the problem that they are not sufficiently stable under the processing conditions of commercial pelleting operations to allow economical use of such pelleting techniques.

Accordingly, even though partial solutions to the problem of enzyme stability during feed processing are available, none of them solves the problem in a totally effective manner.

SUMMARY OF THE INVENTION

It is an object of the invention to provide for a novel xylanase having significant activity at low pH and high temperature.

It is a further object of the invention to provide a novel method for bleaching lignocellulosic pulp.

It is a further object of the invention to provide improved means of treating feed grains to improve their digestibility.

According to the present invention, a purified xylanase is provided which is characterized by the following physical properties: a pH optimum of about 3.6 to 4.2 and a molecular weight of about 50–55 kD as determined by gel filtration. Preferably, the xylanase is derived from Acidothermus sp., more preferably from *Acidothermus cellulolyticus* and most preferably from *Acidothermus cellulolyticus* ATCC 43068.

In a composition embodiment of the invention, a purified xylanase composition is provided, which xylanase is derived from Acidothermus sp. and has a pH optimum of about 3.6 to 4.2 and a molecular weight of about 50–55 kD, as determined by gel filtration.

In another composition embodiment of the invention, a feed additive is provided wherein said feed additive comprises a xylanase derived from Acidothermus sp. and has a pH optimum of about 3.6 to 4.2 and a molecular weight of about 50–55 kD, as determined by gel filtration.

In a method embodiment of the present invention, xylanase isolated from a fermentation culture of Acidothermus sp. is used in the bleaching of a lignocellulosic pulp.

In another method embodiment of the present invention, a feed additive comprising a xylanase derived from Acidothermus sp. having a pH optimum of about 3.6 to 4.2 and a molecular weight of about 50–55 kD, as determined by gel filtration is used to improve the quality of a grain based animal feed.

DETAILED DESCRIPTION OF THE INVENTION

Figure 1:
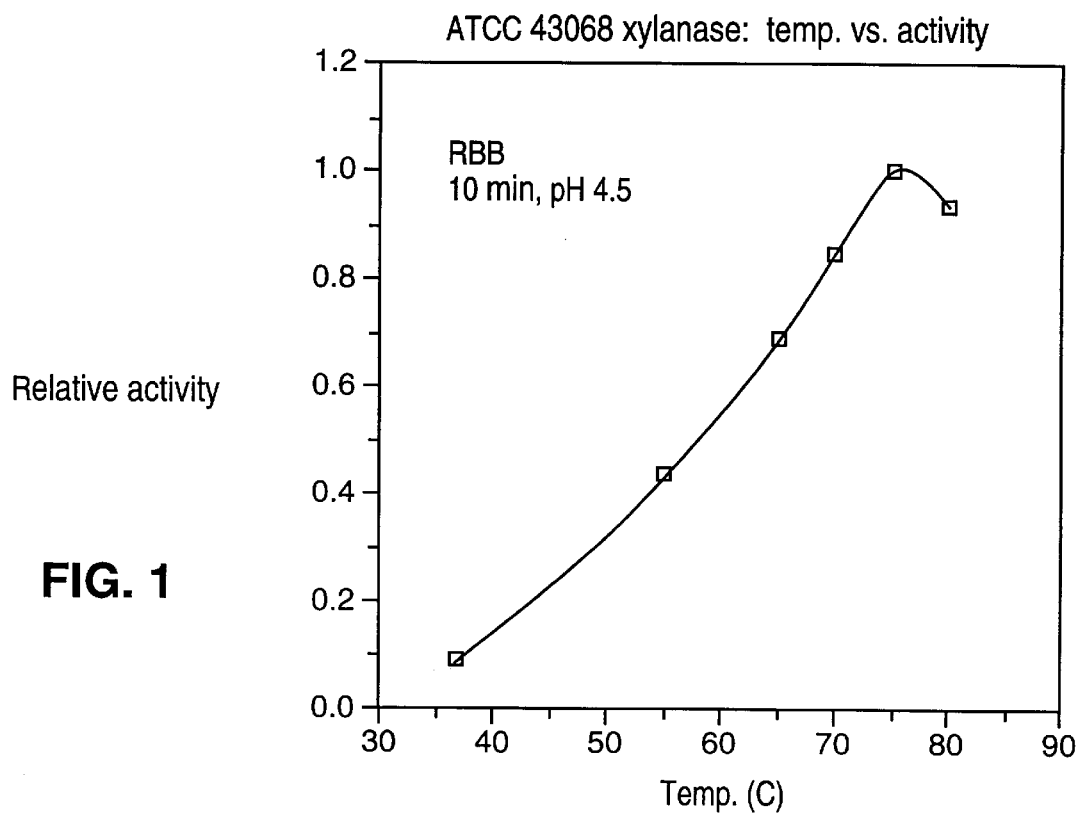
FIG. 1 illustrates the temperature dependency of activity of xylanase according to the invention on RBB-xylan at a pH of 4.5 for 10 minutes.

According to the present invention, a purified xylanase is provided which is characterized by the following physical properties: a pH optimum of about 3.6 to 4.2, a molecular weight of about 50–55 kD as determined by gel filtration, a pI of about 6.0–6.5, and a temperature optimum of about 70–80° C. Preferably, the xylanase is derived from Acidothermus sp., more preferably from *Acidothermus cellulolyticus* and most preferably from *Acidothermus cellulolyticus* ATCC 43068 (deposited with the American Type Culture Collection, 10801 University Boulevard, Manassas, Va., USA 20110). *Acidothermus cellulolyticus* is taxonomically described in Int. J. Systematic Bact., vol. 36, pp. 435–443 (1986) and in U.S. Pat. No. 5,366,884, which are herein incorporated by reference.

In another aspect of the invention, the xylanase derived from Acidothermus sp., and preferably from *Acidothermus cellulolyticus*, is used in the preparation of a cereal based animal feed. In such a cereal-based feed, the cereal is preferably at least one of wheat, barley, maize, sorghum, rye, oats, triticale and rice. It is particularly preferred that the cereal should be wheat.

The cereal-based feed according to the present invention may be provided to animals such as turkeys, geese, ducks, sheep and cows. It is however particularly preferred that the feed is provided to pigs or to poultry, and in particular broiler chickens. The cereal-based feed preferably includes 0.00001–10 g of xylanase protein per kilo of the feed; more preferably includes about 0.0001–1 g of xylanase protein per kilo of the feed; and most preferably 0.001–0.1 g of xylanase protein per kilo of the feed. The cereal-based feed comprises at least 20% by weight of cereal. More preferably, it should include at least 30% by weight of the cereal, and most preferably at least 50% by weight of the cereal. The cereal can be any of those previously mentioned, with wheat being particularly preferred.

Although the cereal component of a cereal-based feed constitutes a source of protein, it is usually necessary to include sources of supplementary protein in the feed such as those derived from fish-meal, meat-meal or vegetables. Sources of vegetable proteins include at least one of full fat soybeans, rapeseeds, canola, soybean-meal, rapeseed-meal and canola-meal. As compared to conventional feeds, the relative amount of the additional protein sources such as fish-meal, meat-meal or vegetable protein can be reduced by adopting the teaching of the present invention resulting in significant cost savings. This is because the relative cost of cereals is significantly less than that of conventional protein supplements. In view of this, a feed can be prepared according to the teaching of the present invention having the same nutritional value in terms of available energy, amino acids and protein as a conventional feed but which includes a higher relative proportion of cereal and a lower relative proportion of protein supplements. It is also found that the inclusion of a thermostable xylanase in an animal feed has the effect that reduced levels of energy supplements such as fats and oils need to be included in order to achieve a feed having a certain level of performance.

The inclusion of a thermostable xylanase in an animal feed in accordance with the present invention enables the crude protein value and/or digestibility and/or amino acid content and/or digestibility coefficients of the feed to be increased, which permits a reduction in the amounts of alternative protein sources and/or amino acids supplements which had previously been necessary ingredients of animal feeds. When the protein digestibility coefficient and/or the content of available crude protein of wheat is increased by the addition of the thermostable xylanase, major savings can be found in the reduced levels of protein and/or energy supplements which have conventionally needed to be added. Alternatively, when only the amino acid content or digestibility coefficient values are increased by the addition of the thermostable xylanase, the major savings are to be found in the reduced levels of amino acid supplements which have conventionally needed to be added to the feeds.

The feed provided by the present invention may also include other enzyme supplements such as one or more of β-glucanase, glucoamylase, mannanase, α-galactosidase, phytase, lipase, α-arabinofuranosidase, protease, α-amylase, esterase, oxidase, oxido-reductase and pectinase. It is particularly preferred to include a protease as a further enzyme supplement such as a subtilisin derived from the genus Bacillus. Such subtilisins are for example described in detail in U.S. Pat. No. 4,760,025.

A suitable feed in accordance with the present invention can be obtained by preparing a feed additive comprising a physiologically acceptable carrier and the thermo-stable xylanase, and then mixing this additive in amounts of 0.01–50 g per kilo with the other components constituting the animal feed (including the cereal and other sources of protein supplement), more preferably 0.1–10 g/kg and most preferably about 1 g/kg.

The physiologically acceptable carrier in this aspect of the present invention is preferably a cereal or derived from a cereal. Such cereals include milled wheat, maize, soya, sugars, starches or a by-product of any of these. Such carriers are conventional in this technical art, and so are not described in any further detail.

The feed additive according to this aspect of the present invention is combined with other feed components to produce a cereal-based feed. Such other feed components include one or more other (preferably thermostable) enzyme supplements, vitamin feed additives, mineral feed additives and amino acid feed additives. The resulting (combined) feed additive including possibly several different types of compounds can then be mixed in an appropriate amount with the other feed components such as cereal and protein supplements to form an animal feed. Processing of these components into an animal feed can be performed using any of the currently used processing apparatuses such as a double-pelleting machine, a steam pelleter, an expander or an extruder.

The presence of the thermostable xylanase in the resulting cereal-based feed has the effect of reducing its FCR. The xylanase may alternatively or additionally increase the digestibility of the cereal-based feed. Further the inclusion of the xylanase may additionally or alternatively increase the rate of bodyweight gain in an animal per unit amount of feed which the animal consumes.

In another embodiment, the xylanases of the present invention have applications in enhancing the delignification and/or the bleaching of pulp according to art-recognized techniques. The process comprises contacting the pulp with whole supernatant xylanase, or one or more of the above described purified xylanases and is dependent upon factors such as pH, temperature, treatment time, dosage of enzyme and the quantity and type of pulp.

It is preferred that the above process be carried out at a temperature and pH which will enhance the enzymatic activity. Temperatures may range from approximately 50–90° C., with 70–85° C. being preferred. The preferred pH for the process ranges from about 5–11, preferably from about, most preferred above 7 to about 9. It is characteristic for the purified xylanases of the present invention to be active over a wide alkaline pH-range as well as having high activity at the preferred pH range of about 7 to about 9.

The preferred treatment period for applying the purified xylanases of the present invention is from about 30 minutes to about 4 hours depending upon factors such as the results desired, the quantity and quality of pulp treated and concentration of enzyme, for example.

A suitable enzyme dosing is about 0.10 to 200 units/g of dry pulp more preferably 0.50 to 50 units/g. The xylanase activity of the enzyme preparations is determined as follows: To 1.8 ml of xylan solution (0.6% Sigma No. X-0627, prepared in 0.05 M sodium acetate buffer and adjusted to pH 5.3 with acetic acid), 0.200 ml of suitably diluted enzyme in the same buffer is added. The solution is incubated at 40° C. for exactly 30 minutes. The reaction is then stopped by adding 3 ml DNS reagent (3,5-dinitrosalicylate 10 g/l; Na,K tartrate 300 g/l), and the color is developed by boiling the sample for 5 minutes. The absorbency is then measured at a wave length of 540 nm. One enzyme unit liberates one micromole of reducing sugars calculated as xylose per minute under assay conditions. The activity is calculated from an enzyme dilution liberating 4 micromoles of reducing sugar under assay conditions.

The present invention may be applied to upgrade or assist in the upgrading of any of a wide variety of processed pulps, i.e., pulps which have been already previously treated in any of a variety of ways to reduce their lignin content and are treated in the process according to the invention to further enhance the lignin removal by chemical methods. The present invention may be applied to treat hardwood and softwood kraft pulps to enhance lignin removal and brightening of the pulps. The invention is particularly applicable to chemical pulps, i.e., those in which the lignin component has been chemically modified by various chemical treatments such as in the sulfate (kraft) processes and oxygen delignification, and is preferably applied to kraft pulps. In a preferred method, the enzymes of the present invention are applied to the pulp after kraft digestion or oxygen delignification but prior to bleaching. In the case where both kraft digestion and oxygen delignification are performed on the same pulp, the enzyme is applied after kraft digestion, prior to oxygen delignification or after oxygen delignification. The present invention is also applicable to ozone bleached pulps.

The resulting pulp is treated to remove the releasable lignin component using an appropriate extractant. In another embodiment, pulp treated with the enzymes of the present invention may be subsequently treated with lignin-degrading chemicals such as chlorine, chlorine dioxide and peroxide, and further extracted with an appropriate extractant. In yet another embodiment, the enzyme treated pulp may be treated with an appropriate extractant, followed by lignin degradation and a final treatment with an appropriate extractant. Such extractants essentially solubilize the affected lignin component and suitable extractants include but are not limited to bases such as alkali metal hydroxides (E), DMF, dioxane, acetone, and alcohol. Hydroxide extractions may be combined with hydrogen peroxide ($E_p$) or oxygen ($E_o$). The resulting pulp may then be further bleached by a chemical bleaching sequence such as chlorine dioxide (DED) or peroxide (P—P) to the desired brightness whereby substantial savings of chemicals are observed when compared to pulp bleached to the same brightness by the same sequence but without using the enzyme treatment. Reduction of chlorine containing chemicals or peroxide is achieved in such a way. In addition, by performing the present invention with the above presented enzymes, one may apply the same amount of bleaching chemicals to the pulp and yet achieve a greater brightness in the treated pulp.

In another embodiment, the present invention provides for additional applications of the purified enzymes described above or whole xylanase supernatant containing xylanases according to the present invention in a variety of industrial settings. For example, the purified xylanases or whole xylanase supernatant may be used to enzymatically breakdown agricultural wastes for production of alcohol fuels and other important industrial chemicals or as a component in a detergent composition.

EXAMPLES

Example 1

Purification of *Acidothermus Xylanase*

*Acidothermus cellulolyticus* ATCC 43068 was obtained from the American Type Culture Collection in Rockville Md. A culture filtrate was obtained by the culturing of the strain in a medium containing: Henssen media (Henssen medium (g/L)

| | | |
|---|---|---|
| K2HPO4 | 0.2 | g |
| MgSo4.7H2O | 0.3 | g |
| CaCO3 | 0.2 | g |
| FeSo4.7H2O | 0.005 | g |
| Yeast extract | 0.1 | g |
| Casamino acid | 0.1 | g |
| NH4HO3 | 0.2 | g |
| Urea | 0.1 | g |
| Asparagine | 0.25 | g |
| Casein | 0.2 | g |
| pH | 5.5 | | with the addition of oat spelt xylan (1%) at a pH of 5.5 and a temperature of 55–60° C. in a 250 ml Erlenmeyer flask at 100 rpm, for 6–8 days. The culture supernatant was subjected to ultrafiltration to concentrate the supernatant including extra cellular xylanase enzyme with the pellet discarded. As described below, the supernatant included significant xylanase activity.

Example 2

Determination of Characteristics of *Acidothermus Xylanase*

Purified xylanase obtained as described above in Example 1 was used to determine the characteristics of the xylanase.
MOLECULAR WEIGHT
Culture supernatant containing xylanase activity was concentrated 4× using Centriprep 3 ultrafiltration cells (Amicon, as per manufacturer instructions). Using a Pharmacia FPLC system, 1 ml concentrated material was applied to two gel filtration columns linked in tandem (Pharmacia Superdex G-200 10/30 followed by Pharmacia Superdex G-75 10/30) which had been equilibrated with 100 mM NaCl-50 mM citrate/phosphate buffer, pH 6.0. Flow rate was 0.5 ml/min., UV absorption was monitored at 280 nm, 1 ml fractions were collected.

Fractions were assayed for xylanase activity as follows: The presence of xylanase was determined using a remazol brilliant blue dyed birchwood xylan (RBB-xylan, Megazyme, Australia) substrate. 50 ul samples are mixed with 400 ul of substrate solution (1.25% [w/v] RBB-xylan in 50 mM sodium acetate, pH 4.5) and incubated at 40° C. for 10 minutes. Undigested xylan is precipitated by the addition of 1 ml 95% ethanol and removed by centrifugation. Released dye remaining in solution is quantified by spectrophotometry ($OD_{590}$) and is proportional to xylanase activity. Activity may be quantified using a standard curve and is reported as XAU/ml (xylanase activity units per milliliter). Xylanase activity was found to elute after 42 minutes using this system. Pharmacia low molecular weight gel filtration standards (1.25 mg/ml) were applied to the system using the above conditions and elution results were used to create a molecular weight standard curve. Elution of *Acidothermus xylanase* corresponded to a molecular weight between 50–55 kilodaltons, (approx. 52.9 kilodaltons) when compared to the standard curve.
ISOELECTRIC POINT
A gel overlay method was used to determine the isoelectric point (pl) of *Acidothermus xylanase*. Isoelectric focusing (IEF) of culture supernatant containing xylanase activity was carried out using a PhastSystem (Pharmacia) as per manufacturer's instructions. IEF gels, pH 3–9, were overlaid with a melted agarose-substrate suspension (0.4% (w/v) agarose, 7 mg/ml RBB-xylan, 0.5% (v/v) glycerol in 50 mM sodium acetate, pH 4.5) and incubated at 37° C. After 1 hour xylanase activity was evident as a clearing zone. Gels were allowed to dry completely and stored. Xylanase pl was determined by comparison with identically run IEF gels containing silver stained pI markers (broad pI kit pH 3.5–9.3, Pharmacia Biotech). Visualization of proteins was by Phast-System development silver staining, as per instructions.

pH AND TEMPERATURE PROFILE

Figure 2:
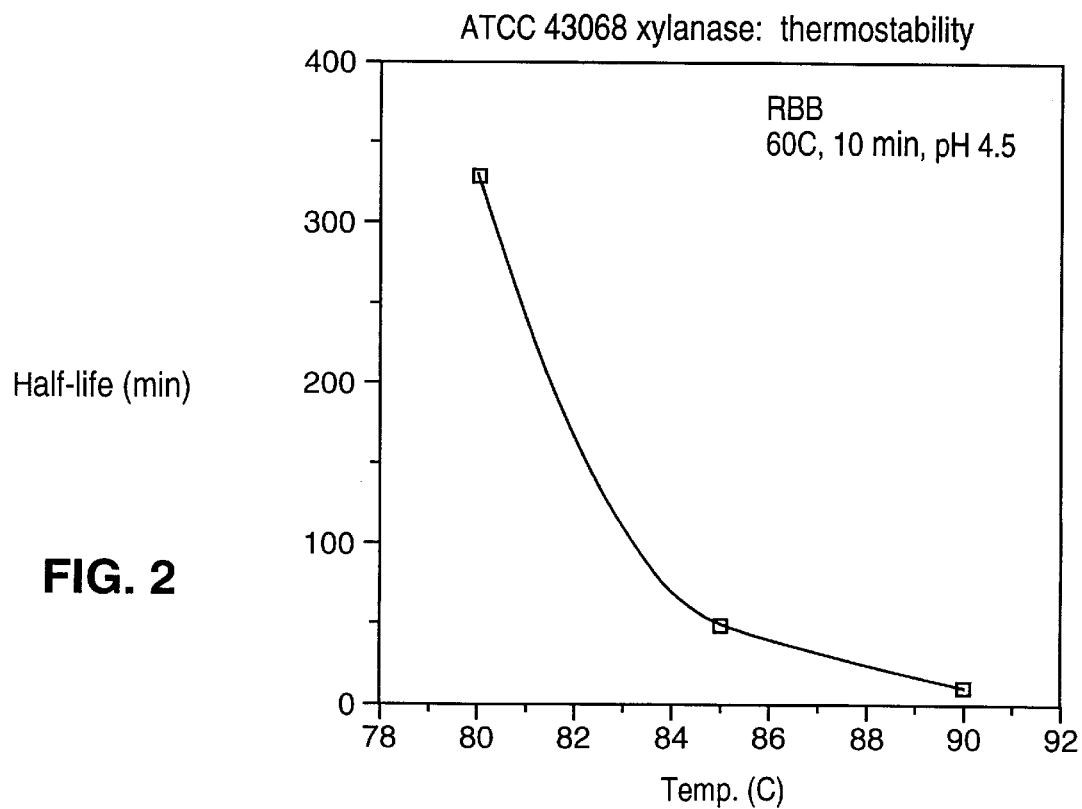
FIG. 2 illustrates the half-life of xylanase treated at a range of temperature.
Figure 3:
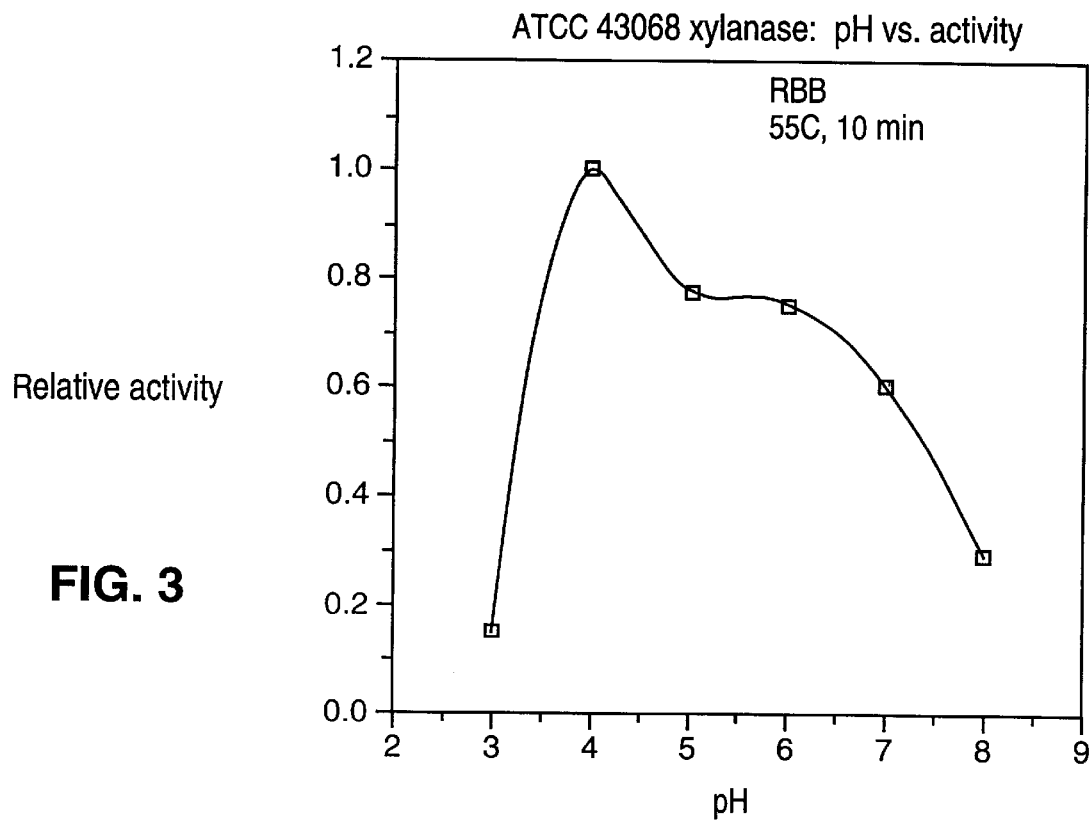
FIG. 3 illustrates the relative activity of xylanase of the invention at a range of pH and depicting the pH optimum.

Enzyme samples were assayed using the RBB-xylan assay as described above in this Example. The pH profile of the purified xylanase was determined by carrying out the RBB assay at pH's of 3.0, 4.0, 5.0, 6.0, 6.0 and 7.0. As shown in FIG. 2, the purified xylanase has a pH optimum under the conditions of the assay of about 3.6–4.2.

Temperature profile of the xylanase was determined by carrying out the RBB-xylan assay at pH 4.5 and a temperature of 37° C., 55° C., 65° C., 70° C. and 80° C. for a period of 10 minutes. As shown in FIG. 1, the purified xylanase has an optimum temperature under the conditions of the assay of between about 70–80° C.

THERMOSTABILITY

Separate samples of purified xylanase were incubated at temperatures of 70° C., 75° C., 80° C., 85° C. or 90° C. Aliquots were taken at certain time intervals to determine the activity of the xylanase after a given time of incubation at the given temperature. The aliquots were assayed for activity according to the RBB-xylan assay at 60° C., pH 4.5 and a time of 10 minutes and the half-life of the xylanase at the incubation temperatures calculated. Results are shown in FIG. 2, half lives at 70° C. and 75° C. under the conditions of the experiment were greater than 24 hours.

LOW pH STABILITY

Figure 4:
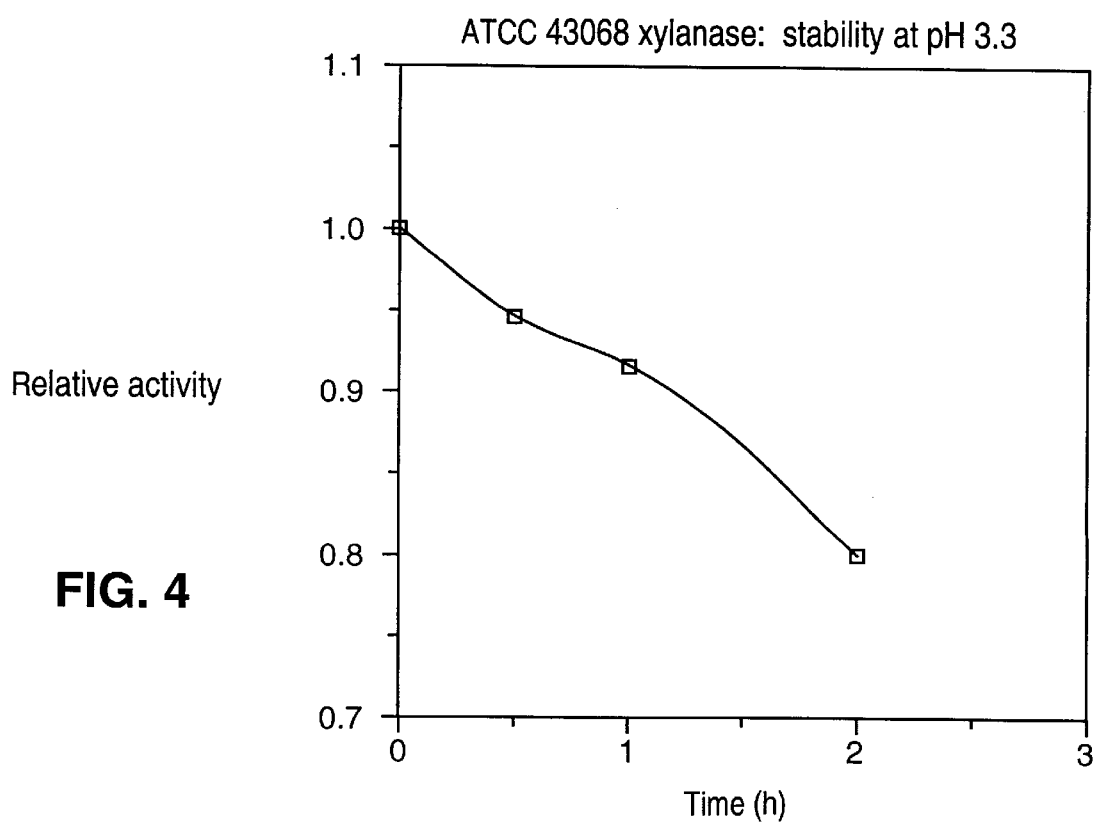
FIG. 4 illustrates the stability of xylanase of the invention over time after treatment at a pH of 3.3.

A purified sample of xylanase as described in Example 2 was adjusted to a pH of 3.3 with sodium hydroxide and incubated at RT. The activity of the sample was measured at 30, 60, 90 and 120 minutes using the RBB assay described above at 65° C., pH of 4.5 for 10 minutes. As shown in FIG. 4, a significant portion of the activity of the xylanase remained after 2 hours at low pH.

Example 3

Treatment of Animal Feed With *Acidothermus Xylanase*

The assay used for xylanase activity was an in vitro viscosity-reducing assay using wheat arabinoxylan as a viscous substrate under conditions which mimic those found in the GI tract of an animal. Such an in vitro assay acts as a guide as to whether a xylanase (or mixture of xylanases) would have the desired effect of reducing digesta viscosity if used as a supplement in an animal feed. Activity was determined as follows:

One unit of xylanase activity is the amount of enzyme which liberates one $\mu$mol of reducing sugars (expressed as xylose equivalents) from the substrate in one minute under the conditions described.

Reagents 1. 1% (w/v) xylan substrate

Add 10 ml of 0.5 M sodium hydroxide to 1.0 g of xylan (Fluka 95590). Mix for 30 minutes with a magnetic stirrer. Add about 40 ml of 0.05 M sodium acetate buffer, pH 6.5. Adjust pH to 6.5 with 1 M acetic acid. Fill to 100 ml with 0.05 M sodium acetate buffer, pH 6.5. Substrate should be mixed all the time when used.

2. 1 M acetic acid

Pipette 5.7 ml of glacial acetic acid into a volumetric flask and fill to 100 ml with distilled water.

3. 0.05 M sodium acetate buffer, pH 6.5

A. Dissolve 4.1 g of sodium acetate in distilled water and fill to 1000 ml with distilled water.

B. Dissolve 3.0 g of glacial acetic acid in distilled water and fill to 1000 ml with distilled water.

Adjust the pH of solution A to pH 6.5 with solution B.

4. Dinitrosalicylic acid (DNS) reagent

Suspend 20.0 g of 3,5-dinitrosalicylic acid in about 800 ml of distilled water. Add gradually 300 ml of sodium hydroxide solution (32.0 g NaOH in 300 ml of distilled water) while stirring continuously. Warm the suspension in a water bath (the temperature may not exceed +48° C.) while stirring until the solution is clear. Add gradually 600 g of potassium sodium tartrate. Warm the solution (the temperature may not exceed +48° C.) if needed until the solution is clear.

Fill to 2000 ml with distilled water and filter through a coarse sintered glass filter.

Store in a dark bottle at room temperature. The Reagent is stable for a maximum of 6 months.

Procedure

1. Enzyme sample 1 ml of enzyme dilution (in 0.05 M sodium acetate buffer, pH 6.5) is equilibrated at +50° C. Add 1 ml of xylan substrate, stir and incubate at +50° C. for exactly 30 minutes. Add 3 ml of DNS-reagent, stir and boil the reaction mixture for exactly 5 minutes. Cool the reaction mixture in a cold water bath to room temperature and measure the absorbance at 540 nm against distilled water.

2. Enzyme blank

Incubate 1 ml of xylan substrate at +50° C. for 30 minutes. Add 3 ml of DNS-solution and stir. Add 1 ml of enzyme dilution (in 0.05 M sodium acetate buffer, pH 6.5) and stir. Boil the mixture for exactly 5 minutes. Cool the reaction mixture in a cold water bath to room temperature and measure the absorbance at 540 nm against distilled water.

The absorbance difference between the enzyme sample and enzyme blank should be 0.3–0.5.

3. Standard curve

Prepare standard solutions from anhydrous xylose in 0.05 M sodium acetate buffer, pH 6.5. Xylose concentration in the standards should be 0.05–0.5 mg/ml. Pipette 1 ml of standard solution, 1 ml of xylan substrate and 3 ml of DNS-reagent into a test tube. Stir and boil for exactly 5 minutes. Cool in a cold water bath to room temperature and measure the absorbance at 540 nm against standard blank. In the standard blank, xylose solution is replaced by 1 ml of 0.05 M sodium acetate buffer, pH 6.5. Otherwise standard blank is treated like xylose standard.

Plot xylose concentration as a function of absorbance. New standard curve is prepared for every new DNS-reagent.

Calculation

The xylanase activity of the sample is calculated according to the following equation:

$$\text{Activity (U/g)} = \frac{([A(X) - A(O)] \times k + C_o) \times 1000 \times Df}{MW_{xyl} \times t}$$

wherein:

A(X)=absorbance of the enzyme sample

A(O)=absorbance of the enzyme blank k=the slope of the standard curve $C_o$=the intercept of xylose standard curve 1000=factor, mmol $\rightarrow$ $\mu$mol Df=dilution factor (ml/g)

$MW_{xyl}$=molecular weight of xylose (150.13 mg/mmol)

t=reaction time (30 minutes)

The viscosity-reducing assay used to measure the ability of a xylanase to reduce viscosity was carried out as follows. The assay is carried out in all cases in duplicate.

The xylanase enzyme to be assayed is diluted with 0.1 M Na-phosphate buffer having a pH of 6.5 in order to adjust the xylanase concentration so that the resulting solution possesses a xylanase activity of 1.0 unit per ml. Such xylanase activity is determined according to the assay method for xylanase activity described in detail above.

100 μl of the enzyme solution was added to 400 μl of a solution of wheat arabinoxylan (obtained from Megazyme Pty) in 0.1 M Na-phosphate at pH 6.5 in a glass test tube so that the final concentration of enzyme in the resulting solution was 0.2 U/ml and that of the wheat arabinoxylan was 1.0% w/w.

The test tubes containing the solutions were then sealed and placed in a water-bath set at 95° C. for a certain period of time, typically 1 minute or 5 minutes. After this heat treatment, the test tubes were cooled in an ice-water bath. The viscosity of the resulting solution was measured at a temperature of 40° C. using a Brookfield DV-II, CP 40 viscometer programmed to measure viscosity once a second. The figures shown in Table 1 are viscosity measurements after 20 minutes of incubation. Xylanase from *Acidothermus cellulolyticus* was compared with xylanase from *Aspergillus niger* and *Trichoderma viride*, two well known additives for feed. The results were as follows:

TABLE 1

| Xylanase Source | Viscosity - (Pa.s) no heat treatment (Control) | Viscosity (Pa.s) 20 minutes after exposure to 95° C. for 1 minute | Viscosity (Pa.S) 20 minutes after exposure to 95° C. for 5 minutes |
|---|---|---|---|
| *Trichoderma viride* | $2.0 \times 10^{-3}$ | $1.1 \times 10^{-2}$ | $1.1 \times 10^{-2}$ |
| *Aspergillus niger* | $1.4 \times 10^{-3}$ | $7.2 \times 10^{-3}$ | $7.3 \times 10^{-3}$ |
| *Acidothermus cellulolyticus* | $4.3 \times 10^{-3}$ | $4.0 \times 10^{-3}$ | $9.9 \times 10^{-3}$ |

As shown in Table 1, exposure to a temperature of 95° C. for one minute resulted in essentially no increase in the viscosity level with xylanase derived from *Acidothermus cellulolyticus*, while significant increases in viscosity were shown with the xylanases from *Aspergillus niger* and *Trichoderma viride*. Similarly, the increase in viscosity after exposure to a temperature of 95° C. for five minutes of xylanase from *Acidothermus cellulolyticus* was less than half of that of the xylanases derived from *Aspergillus niger* and *Trichoderma viride*.

Of course, it should be understood that a wide range of changes and modifications can be made to the preferred embodiments described above. It is therefore intended to be understood that it is the following claims, including all equivalents, which define the scope of the invention.

We claim:

1. A purified xylanase having a pH optimum of about 3.6 to 4.2 and a molecular weight of about 50–55 kD as determined by gel filtration obtained from *Acidothermus cellulolyticus*.

2. The purified xylanase according to claim 1, wherein said xylanase has a temperature optimum of about 70–80° C.

3. The purified xylanase according to claim 1, wherein said xylanase is obtained from *Acidothermus cellulolyticus* ATCC 43068.

* * * * *